(12) United States Patent
Furuichi et al.

(10) Patent No.: US 9,836,835 B2
(45) Date of Patent: Dec. 5, 2017

(54) IMAGING APPARATUS FOR DIAGNOSIS, INFORMATION PROCESSING APPARATUS, AND CONTROL METHOD THEREOF, PROGRAM THEREOF, AND COMPUTER-READABLE STORAGE MEDIUM THEREOF

(71) Applicant: TERUMO KABUSHIKI KAISHA, Shibuya-ku, Tokyo (JP)

(72) Inventors: Junya Furuichi, Hadano (JP); Kouichi Inoue, Odawara (JP)

(73) Assignee: TERUMO KABUSHIKI KAISHA, Shibuya-ku, Tokyo (JP)

( * ) Notice: Subject to any disclaimer, the term of this patent is extended or adjusted under 35 U.S.C. 154(b) by 162 days.

(21) Appl. No.: 14/842,910

(22) Filed: Sep. 2, 2015

(65) Prior Publication Data
US 2015/0371382 A1 Dec. 24, 2015

Related U.S. Application Data

(63) Continuation of application No. PCT/JP2013/001313, filed on Mar. 4, 2013.

(51) Int. Cl.
*G06T 7/00* (2017.01)
*A61B 8/12* (2006.01)
(Continued)

(52) U.S. Cl.
CPC ............ *G06T 7/0012* (2013.01); *A61B 5/004* (2013.01); *A61B 5/0066* (2013.01);
(Continued)

(58) Field of Classification Search
CPC ............... G06T 7/0012; G06T 2200/04; G06T 2207/10101; G06T 2207/10136;
(Continued)

(56) References Cited

U.S. PATENT DOCUMENTS 5,054,492 A 10/1991 Scribner et al.
7,738,941 B2 6/2010 Hirota
(Continued)

FOREIGN PATENT DOCUMENTS

JP 6-030937 A 2/1994
JP 7-116166 A 5/1995
(Continued)

OTHER PUBLICATIONS

Extended European Search Report dated Oct. 12, 2016 by the European Patent Office in corresponding European Patent Application No. 13877170.4 (7 pages).
(Continued)

*Primary Examiner* — Amandeep Saini
(74) *Attorney, Agent, or Firm* — Buchanan Ingersoll & Rooney PC

(57) ABSTRACT

A technique is disclosed for helping prevent image quality of a three-dimensional image from becoming poor due to fluctuations in the rotation speed of an imaging core. For this purpose, if data is obtained from the imaging core by moving and rotating the imaging core, a cross-sectional image is generated at each movement position. Then, a direction where a guidewire is present in each of the cross-sectional images is detected. An angular difference between the direction of the detected guidewire and a preset direction is obtained so as to rotate each of the cross-sectional images in accordance with the angular difference. Then, the cross-sectional images which are previously rotated in this way are connected to one another, thereby generating the three-dimensional image.

20 Claims, 8 Drawing Sheets

(51) Int. Cl.
*A61B 8/08* (2006.01)
*A61B 8/00* (2006.01)
*A61B 5/00* (2006.01)
*A61B 8/14* (2006.01)

(52) U.S. Cl.
CPC .......... *A61B 5/0084* (2013.01); *A61B 5/6876* (2013.01); *A61B 8/0891* (2013.01); *A61B 8/12* (2013.01); *A61B 8/4416* (2013.01); *A61B 8/4461* (2013.01); *A61B 8/5276* (2013.01); *A61B 5/0035* (2013.01); *A61B 8/14* (2013.01); *A61B 8/445* (2013.01); *A61B 8/483* (2013.01); *A61B 2576/02* (2013.01); *G06T 2200/04* (2013.01); *G06T 2207/10101* (2013.01); *G06T 2207/10136* (2013.01); *G06T 2207/30104* (2013.01)

(58) Field of Classification Search
CPC ........ G06T 2207/30104; A61B 5/0066; A61B 5/0084; A61B 5/6876; A61B 8/0891; A61B 8/12; A61B 8/4416; A61B 8/4461; A61B 8/5276; A61B 5/0035; A61B 8/14; A61B 8/445; A61B 8/483; A61B 2576/02
USPC ....................................................... 382/131
See application file for complete search history.

(56) References Cited

U.S. PATENT DOCUMENTS

| | | |
|---|---|---|
| 2005/0140984 A1 | 6/2005 | Hitzenberger |
| 2007/0232891 A1 | 10/2007 | Hirota |
| 2010/0094127 A1 | 4/2010 | Xu |
| 2011/0071404 A1 | 3/2011 | Schmitt et al. |
| 2012/0075638 A1 | 3/2012 | Rollins et al. |
| 2012/0170848 A1* | 7/2012 | Kemp ........................ G06T 5/50 382/195 |

FOREIGN PATENT DOCUMENTS

| | | |
|---|---|---|
| JP | 7-184899 A | 7/1995 |
| JP | 11-056752 A | 3/1999 |
| JP | 2007-267867 A | 10/2007 |
| WO | 2012126070 A1 | 9/2012 |

OTHER PUBLICATIONS

International Search Report (PCT/ISA/210) dated Jun. 4, 2013, by the Japanese Patent Office as the International Searching Authority for International Application No. PCT/JP2013/001313.

\* cited by examiner

IMAGING APPARATUS FOR DIAGNOSIS, INFORMATION PROCESSING APPARATUS, AND CONTROL METHOD THEREOF, PROGRAM THEREOF, AND COMPUTER-READABLE STORAGE MEDIUM THEREOF

CROSS-REFERENCES TO RELATED APPLICATIONS

This application is a continuation of International Application No. PCT/JP2013/001313 filed on Mar. 4, 2013, the entire content of which is incorporated herein by reference.

TECHNICAL FIELD

The present disclosure relates to an imaging apparatus for diagnosis which can generate a tomographic image of biological tissues by using ultrasound or light, an information processing apparatus, and a control method thereof, a program thereof, and a computer-readable storage medium thereof.

BACKGROUND DISCUSSION

Intravascular therapy is performed by using a high-function catheter such as a balloon catheter, a stent, or the like. An imaging apparatus for diagnosis such as an optical coherence tomography (OCT) apparatus, an intravascular ultrasound (IVUS) apparatus, and the like has been generally used in order to perform preoperative diagnosis or to check postoperative progress.

The optical coherence tomography apparatus has a built-in optical fiber, to a distal end of which an imaging core having an optical lens and an optical mirror is attached. At least a distal end portion of the optical coherence tomography apparatus has a transparent sheath.

Then, the sheath is inserted into a blood vessel of a patient. While the imaging core is rotated, light is emitted to a vascular wall via the optical mirror. The light reflected from the blood vessel is received again via the optical mirror, and radial scanning is performed, thereby configuring a cross-sectional image of the blood vessel, based on the obtained reflection light. Then, while the optical fiber is rotated, a pulling operation (generally called pulling-back) is performed at a predetermined speed, thereby forming a three-dimensional image of an inner wall in the longitudinal direction of the blood vessel (refer to JP-A-2007-267867). In addition, as an improved OCT type, a swept-source optical coherence tomography (SS-OCT) apparatus which uses a swept-source has also been developed.

In the intravascular ultrasound apparatus, a target to be emitted is ultrasound. That is, the ultrasound is emitted toward biological tissues, and reflected waves from each boundary surface of the biological tissues are detected so as to obtain information of the biological tissues in the emitting direction. The imaging core which emits and detects the ultrasound is rotated, thereby configuring an ultrasound cross-sectional image. Then, pulling-back is performed so as to form a three-dimensional image. Furthermore, a technique for generating a cross-sectional image and a three-dimensional image by applying both ultrasound and light has been known (refer to JP-A-11-56752).

SUMMARY

As described above, in any case of the optical coherence tomography apparatus and the intravascular ultrasound apparatus, a portion of the imaging core which emits light or ultrasound toward biological tissues has a rotating structure. Then, pulling-back is performed, thereby reconfiguring a three-dimensional image of an intravascular wall.

The present disclosure generally relates to a problem of non-uniform rotation distortion (NURD) in the above-described tomography apparatus. This NURD will be described herein by using the optical coherence tomography apparatus as an example.

When diagnosis is performed, a sheath which has an optical fiber whose distal end is provided with an imaging core having an optical lens and an optical mirror, and whose distal end portion is configured to have a transparent member is introduced into a blood vessel of a diagnosis target lesion site. Then, a rear end (base) of the optical fiber is rotated so as to rotate the optical mirror in the imaging core. Since the blood vessel is curved everywhere, the optical fiber can inevitably come into contact with inner walls of the sheath at some locations. This contact can cause frictional resistance to rotation. That is, even if the optical fiber is rotated at constant speed, the rotation speed of the imaging core varies in the rear end of the optical fiber due to the influence of the above-described frictional resistance. A three-dimensional image of an intravascular wall can be obtained by continuously connecting multiple blood vessel cross-sectional images to one another in the longitudinal direction of the blood vessel. Therefore, during the pulling-back, if the rotation fluctuates more than allowed, a difference is generated in each direction of the blood vessel cross-sectional images. Consequently, an obtainable three-dimensional image is not an image which is smooth in the longitudinal direction of the blood vessel. This phenomenon is referred to as the NURD.

In accordance with an exemplary embodiment, a technique is disclosed for helping prevent image quality of a three-dimensional image from becoming poor due to fluctuations in rotation speed of an imaging core.

In accordance with an exemplary embodiment, an imaging apparatus is disclosed for diagnosis which reconfigures a three-dimensional image of biological tissues in such a way that a probe which has a sheath for accommodating an imaging core emitting light or ultrasound toward the biological tissues and detecting a reflected signal of the emitting light or ultrasound and a guidewire for guiding the biological tissues in a distal end is used so as to move and rotate the imaging core along the sheath.

The imaging apparatus for diagnosis can include cross-sectional image generation means for generating a cross-sectional image at each axial position of the movement, based on data obtained via the imaging core by the movement and rotation of the imaging core inside the sheath, detection means for detecting a direction in which the guidewire is present in each of the cross-sectional images, rotation means for performing processing for rotating a target cross-sectional image detected by the detection means in accordance with an angular difference between the direction in which the guidewire is present and a preset direction in the target cross-sectional image, for each of the cross-sectional images and three-dimensional image generation means for generating the three-dimensional image along the movement direction from each of the cross-sectional images which are previously rotated by the rotation means.

An imaging apparatus is disclosed for diagnosis which reconfigures a three-dimensional image of biological tissues in such a way that a probe which has a sheath for accommodating an imaging core emitting a signal toward the biological tissues and detecting a reflected signal thereof and whose distal end has a guidewire lumen for guiding the imaging core to the biological tissues, and a guidewire passing through the inside of the guidewire lumen are used so as to move and rotate the imaging core along the sheath, the imaging apparatus for diagnosis comprising: cross-sectional image generation means for generating a cross-sectional image at each axial position of the movement, based on data obtained via the imaging core by the movement and rotation of the imaging core inside the sheath; detection means for detecting a direction in which the guidewire is present in each of the cross-sectional images; rotation means for performing processing for rotating a target cross-sectional image detected by the detection means in accordance with an angular difference between the direction in which the guidewire is present and a preset direction in the target cross-sectional image, for each of the cross-sectional images; and three-dimensional image generation means for generating the three-dimensional image along the movement direction from each of the cross-sectional images which are previously rotated by the rotation means.

A control method is disclosed of an imaging apparatus for diagnosis which reconfigures a three-dimensional image of biological tissues in such a way that a probe which has a sheath for accommodating an imaging core emitting a signal toward the biological tissues and detecting a reflected signal thereof and whose distal end has a guidewire lumen for guiding the imaging core to the biological tissues, and a guidewire passing through the inside of the guidewire lumen are used so as to move and rotate the imaging core along the sheath, the control method comprising: generating a cross-sectional image at each axial position of the movement, based on data obtained via the imaging core by the movement and rotation of the imaging core inside the sheath; detecting a direction where the guidewire is present in each of the cross-sectional images; rotating a target cross-sectional image detected in the detection step in accordance with an angular difference between the direction in which the guidewire is present and a preset direction in the target cross-sectional image, for each of the cross-sectional images; and generating the three-dimensional image along the movement direction from each of the cross-sectional images which are previously rotated.

An information processing apparatus is disclosed that generates a three-dimensional image, based on data from an imaging core, which is obtained by an imaging apparatus for diagnosis that uses a probe which has a sheath for accommodating the imaging core emitting a signal toward the biological tissues and detecting a reflected signal thereof and whose distal end has a guidewire lumen for guiding the imaging core to the biological tissues, and a guidewire passing through the inside of the guidewire lumen so as to move and rotate the imaging core along the sheath, the information processing apparatus comprising: cross-sectional image generation means for generating a cross-sectional image at each axial position of the movement, based on the data obtained via the imaging core; detection means for detecting a direction in which the guidewire is present in each of the cross-sectional images; rotation means for performing processing for rotating a target cross-sectional image detected by the detection means in accordance with an angular difference between the direction in which the guidewire is present and a preset direction in the target cross-sectional image, for each of the cross-sectional images; and three-dimensional image generation means for generating the three-dimensional image along the movement direction from each of the cross-sectional images which are previously rotated by the rotation means.

A control method is disclosed of an information processing apparatus that generates a three-dimensional image, based on data from an imaging core, which is obtained by an imaging apparatus for diagnosis that uses a probe which has a sheath for accommodating the imaging core emitting a signal toward the biological tissues and detecting a reflected signal thereof and whose distal end has a guidewire for guiding the imaging core to the biological tissues, so as to move and rotate the imaging core along the sheath, the control method comprising: generating a cross-sectional image at each axial position of the movement, based on the data obtained via the imaging core; detecting a direction in which the guidewire is present in each of the cross-sectional images; rotating a target cross-sectional image detected in the detection step in accordance with an angular difference between the direction in which the guidewire is present and a preset direction in the target cross-sectional image, for each of the cross-sectional images; and generating the three-dimensional image along the movement direction from each of the cross-sectional images which are previously rotated.

According to the present disclosure, image quality of a three-dimensional image can be prevented from becoming poor due to fluctuations in rotation speed of an imaging core.

Other characteristics and advantages of the present invention will become apparent from the following description made with reference to the accompanying drawings. In the accompanying drawings, the same reference numerals are given to identical or similar configuration elements.

BRIEF DESCRIPTION OF THE DRAWINGS

The accompanying drawings are incorporated in the description, configure a part of the description, represent embodiments of the present disclosure, and are used to describe principles of the present disclosure together with the description.

DETAILED DESCRIPTION

Hereinafter, an exemplary embodiment of the present disclosure will be described in detail with reference to the accompanying drawings. In the exemplary embodiment, an apparatus having an OCT function will be described as an example of an imaging apparatus for diagnosis. However, it will be apparent from the following description that the embodiment can be applied to not only an apparatus having an IVUS function, but also an apparatus having both the IVUS function and the OCT function.

1. External Configuration of Imaging Apparatus for Diagnosis

Figure 1:
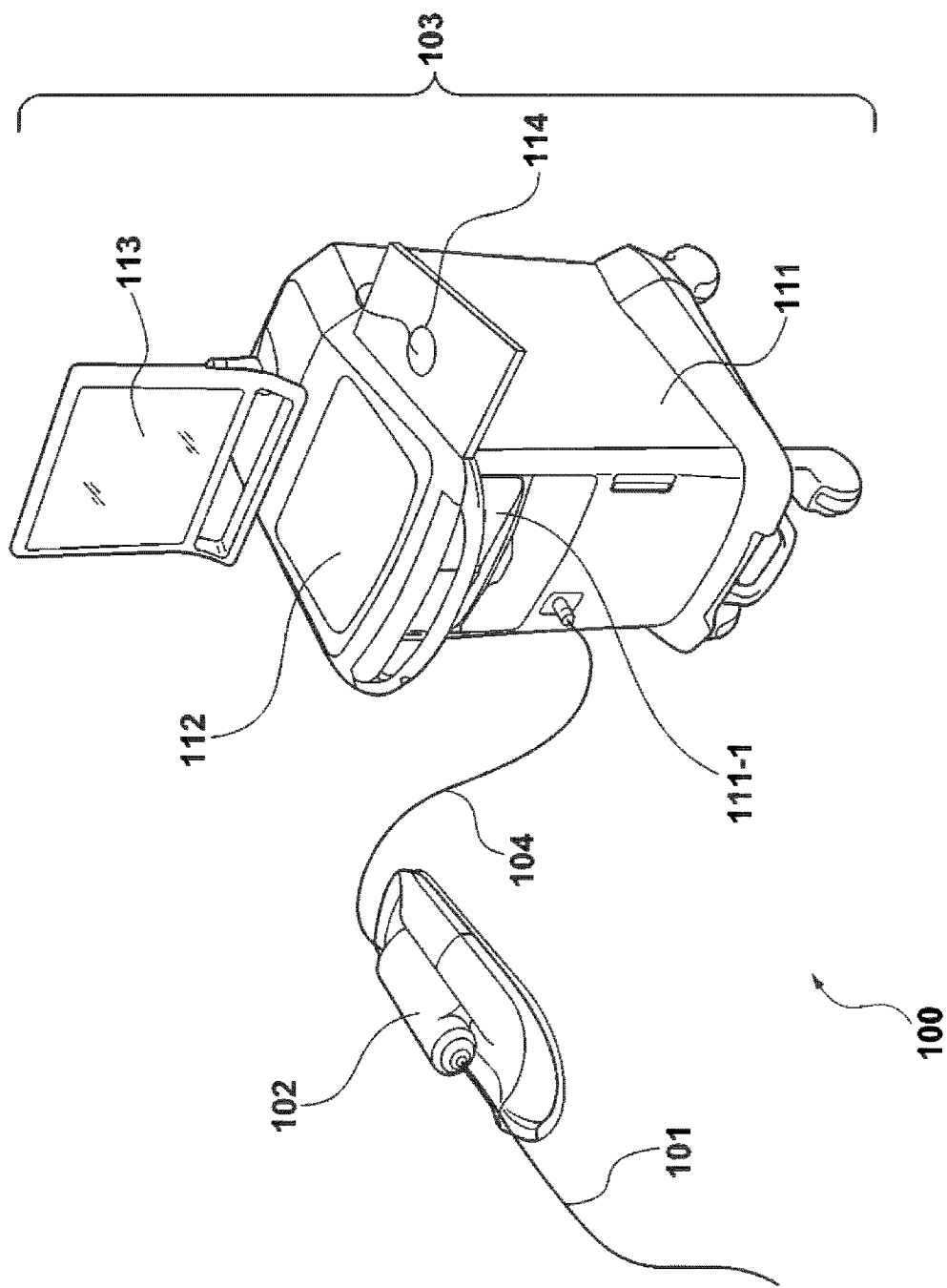
FIG. 1 is a view illustrating an external configuration of an imaging apparatus for diagnosis according to an exemplary embodiment of the present disclosure.

FIG. 1 is a view illustrating an external configuration of an imaging apparatus for diagnosis 100 according to an exemplary embodiment of the present disclosure.

As illustrated in FIG. 1, the imaging apparatus for diagnosis 100 can include a probe unit 101, a scanner and pulling-back unit 102, and an operation control apparatus 103. The scanner and pulling-back unit 102 and the operation control apparatus 103 are connected to each other so that various signals can be transmitted therebetween by a signal line 104.

An imaging core directly inserted into a blood vessel, and provided with an optical transceiver which continuously transmits transmitted light (measurement light) into the blood vessel and continuously receives reflected light from the inside of the blood vessel is inserted into the probe unit 101. The imaging apparatus for diagnosis 100 uses the imaging core so as to measure a state inside the blood vessel.

The scanner and pulling-back unit 102 can be configured so that the probe unit 101 is detachably attached thereto. An operation in the axial direction and an operation in the rotation direction inside the blood vessel of the imaging core inserted into the probe unit 101 can be regulated by driving a built-in motor.

When the measurement is performed, the operation control apparatus 103 is provided with a function for inputting various setting values and a function for displaying the cross-sectional image inside the blood vessel (cross-sectional image in the horizontal direction and cross-sectional image in the vertical direction) after processing data obtained during the measurement.

In the operation control apparatus 103, the reference numeral 111 represents a main body control unit. The main body control unit generates interference light data by causing the reflected light obtained by the measurement to interfere with reference light obtained by splitting the light from a light source, and which performs processing on line data generated based on the interference light data, thereby generating an optical cross-sectional image.

The reference numeral 111-1 represents a printer and DVD recorder, which prints a processing result in the main body control unit 111 or stores the processing result as data. The reference numeral 112 represents an operation panel. A user inputs various setting values and instructions via the operation panel 112. The reference numeral 113 represents an LCD monitor serving as a display apparatus. The LCD monitor displays the cross-sectional image generated in the main body control unit 111. The reference numeral 114 represents a mouse serving as a pointing device (coordinate input device).

Figure 2:
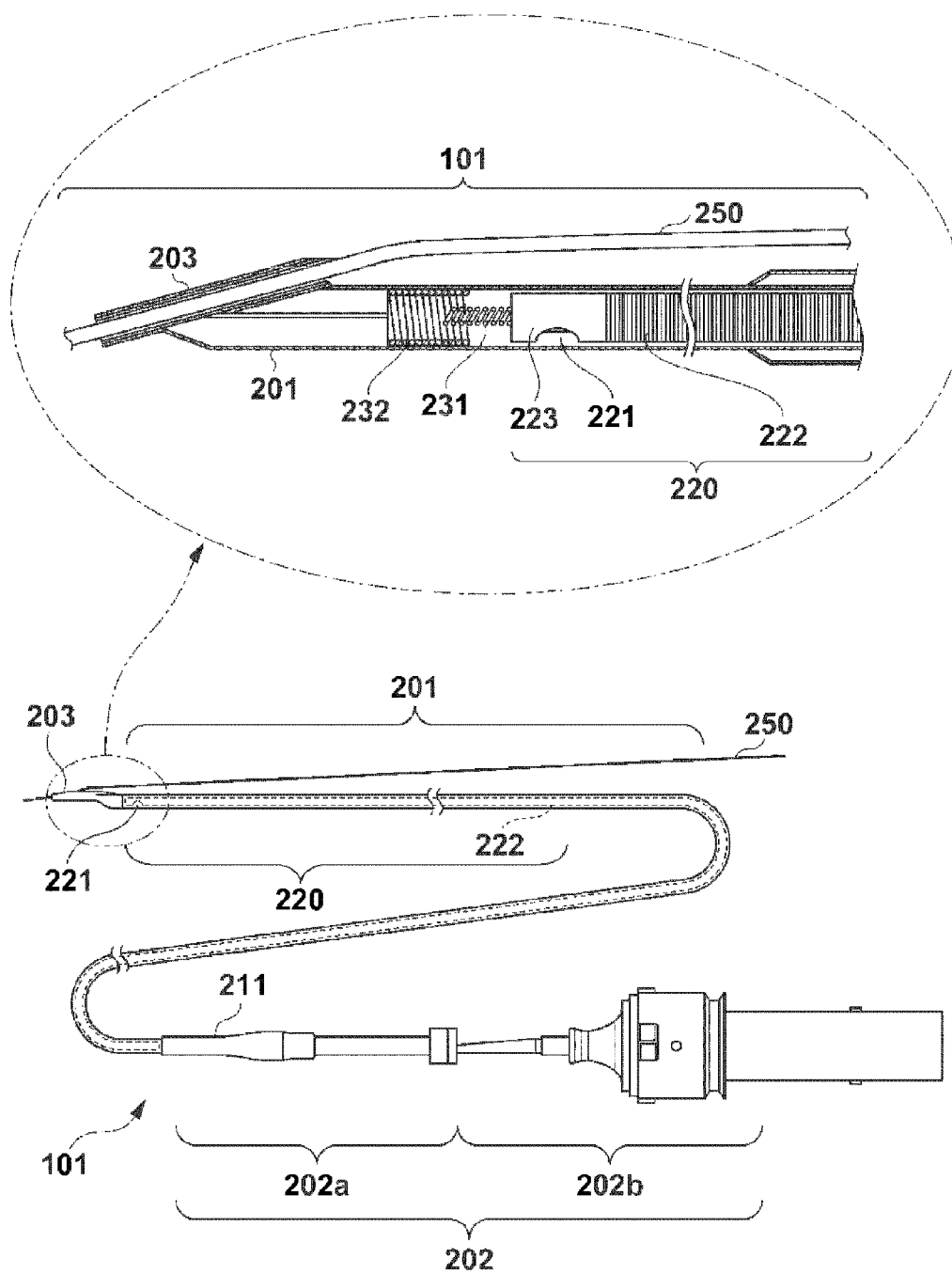
FIG. 2 is a view illustrating an overall configuration of a probe unit and a sectional configuration of a distal end portion.

2. Overall Configuration of Probe Unit and Cross-Sectional Configuration of Distal End Portion Next, an overall configuration of the probe unit 101 and a cross-sectional configuration of a distal end portion will be described with reference to FIG. 2. As illustrated in FIG. 2, the probe unit 101 is configured to have an elongated catheter sheath 201 to be inserted into the blood vessel, and a connector 202 which is not inserted into the blood vessel and which is arranged on a user's hand-side for the user's operation. A guidewire lumen tube 203, which fixes a guidewire 250 for guiding the probe unit 101 to a diagnosis target position in the blood vessel is disposed in a distal end of the catheter sheath 201. The catheter sheath 201 forms a lumen, which is continuous from a connection portion with the guidewire lumen tube 203 to a connection portion with the connector 202.

The lumen of the catheter sheath 201 is internally provided with a transceiver 221 having an optical transceiver arranged in the catheter sheath 201 to transmit and receive light, and an optical fiber cable. An imaging core 220 provided with a coil-shaped drive shaft 222, which transmits a rotational drive force for rotating both of the transceiver and the cable is inserted into the catheter sheath 201 over substantially the entire length of the catheter sheath 201.

The connector 202 is provided with a sheath connector 202a configured to be integrated with the proximal end of the catheter sheath 201 and a drive shaft connector 202b configured to rotatably fix the drive shaft 222 to the proximal end of the drive shaft 222.

An anti-kink protector 211 is disposed in a boundary portion between the sheath connector 202a and the catheter sheath 201, which can maintain a predetermined rigidity in the anti-kink protector 211. Accordingly, bending (kinking) can be prevented which may occur due to an abrupt change in physical properties.

The proximal end of the drive shaft connector 202b can be detachably attached to the scanner and pulling-back unit 102.

A housing 223 has a shape in which a short cylindrical metal pipe has a partially cutout portion, and, for example, is formed by being cut out from a metal ingot, or is molded by means of metal powder injection molding (MIM). In addition, an elastic member 231 having a short coil shape is disposed on the distal end side of the housing 223.

The elastic member 231 can be obtained by forming a stainless steel wire into a coil shape. The elastic member 231 is arranged on the distal end side, thereby preventing the imaging core 220 from being caught on the inside of the catheter sheath 201 when the imaging core 220 is moved forward and rearward.

The reference numeral 232 represents a reinforcement coil, which can help prevent rapid bending of the distal end portion of the catheter sheath 201.

The guidewire lumen tube 203 has a guidewire lumen into which a guidewire 250 can be inserted. The guidewire 250 is used in order to introduce the distal end of the catheter sheath 201 to a lesion site.

3. Functional Configuration of Imaging Apparatus for Diagnosis

Figure 3:
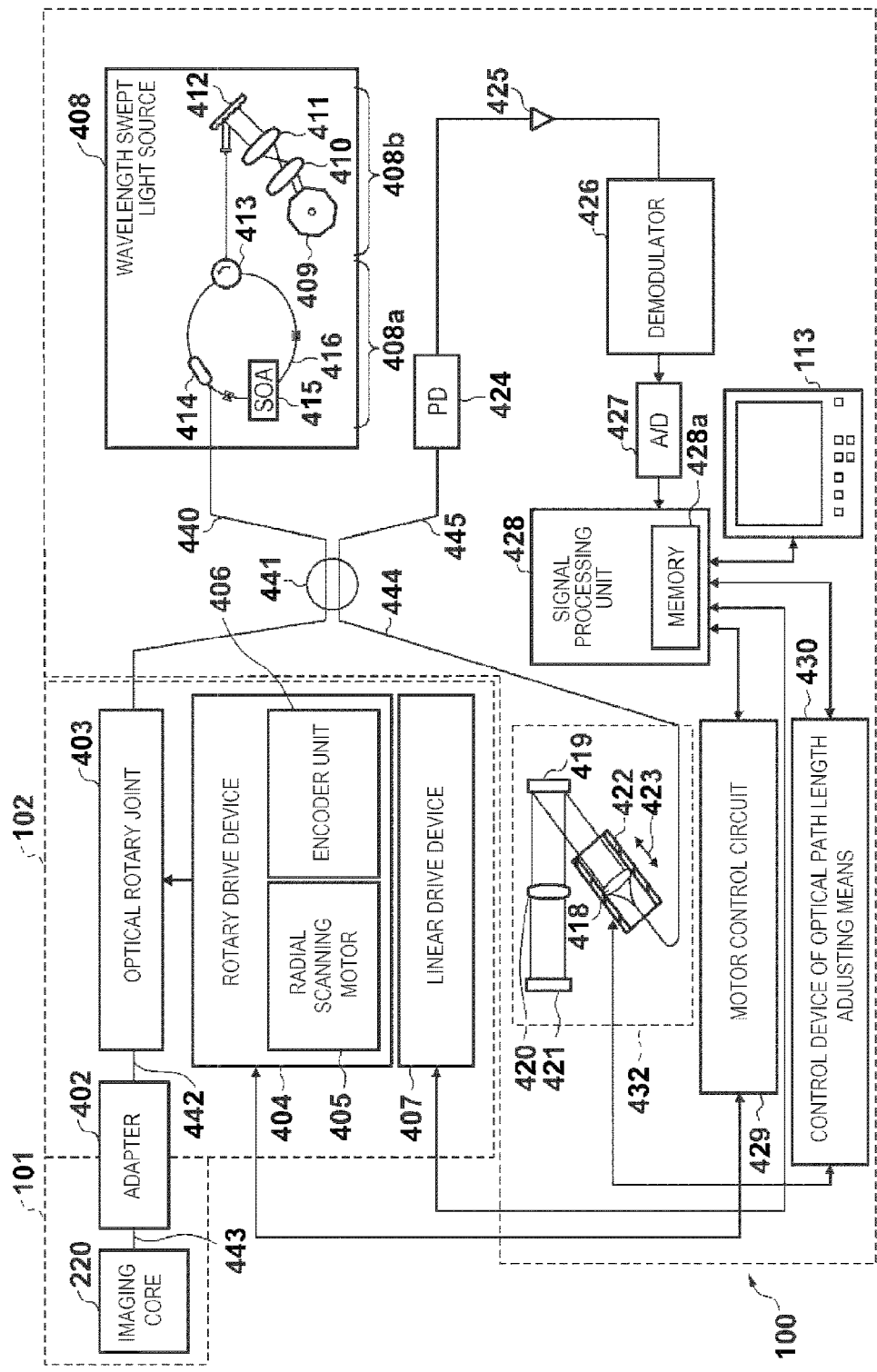
FIG. 3 is a view illustrating a functional configuration of the imaging apparatus for diagnosis.

Next, a functional configuration of the imaging apparatus for diagnosis 100 will be described. FIG. 3 is a view illustrating the functional configuration of the imaging apparatus for diagnosis 100 which has an OCT (here, a swept source OCT as an example) function. Hereinafter, referring to the same drawing, the functional configuration of the swept source OCT will be described.

In the drawing, the reference numeral 408 represents a swept laser, and is one type of an extended-cavity laser which is configured to have an optical fiber 416 coupled to a semiconductor optical amplifier (SOA) 415 in a ring shape and a polygon scanning filter (408b).

Light output from the SOA 415 proceeds to the optical fiber 416, and enters the polygon scanning filter 408b. The light whose wavelength is selected here is amplified by the SOA 415, and is finally output from a coupler 414.

The polygon scanning filter 408b selects the wavelength in combination with a diffraction grating 412 for diffracting the light and a polygon mirror 409. For example, the light diffracted by the diffraction grating 412 is concentrated on a surface of the polygon mirror 409 by two lenses (410 and 411). In this manner, only the light having a wavelength orthogonal to the polygon mirror 409 returns through the same optical path, and is output from the polygon scanning filter 408b. In accordance with an exemplary embodiment, for example, time sweeping of the wavelength can be performed by rotating the polygon mirror 409.

For example, a 32-sided mirror is used for the polygon mirror 409 whose rotation speed is approximately 50,000 rpm. A wavelength swept system in which the polygon mirror 409 and the diffraction grating 412 are combined with each other enables high speed and high output wavelength sweeping.

The light of a wavelength swept light source 408 which is output from the coupler 414 is incident on one end of a first single mode fiber 440, and is transmitted to the distal end side. The first single mode fiber 440 is optically coupled to a second single mode fiber 445 and a third single mode fiber 444 in an optical coupler 441 located in the middle therebetween.

On the further distal end side from the optical coupler 441 of the first single mode fiber 440, an optical rotary joint (optical coupling unit) 403 which transmits the light by coupling a non-rotating part (fixed portion) and a rotating part (rotary drive unit) to each other is disposed inside a rotary drive device 404.

Furthermore, a fifth single mode fiber 443 of the probe unit 101 is detachably connected via an adapter 402 to the distal end side of a fourth single mode fiber 442 inside the optical rotary joint (optical coupling unit) 403. In this manner, the light from the wavelength swept light source 408 can be transmitted to the fifth single mode fiber 443 which is inserted into the imaging core 220 so as to be rotatably driven.

The transmitted light is emitted from the optical transceiver 221 of the imaging core 220 to biological tissues inside the blood vessel while a rotary operation and an axial operation are performed. Then, the reflected light scattered on a surface or inside the biological tissues can be partially captured by the optical transceiver 221 of the imaging core 220, and returns to the first single mode fiber 440 side through a rearward optical path. Furthermore, the light can be partially transferred to the second single mode fiber 445 side by the optical coupler 441, and is emitted from one end of the second single mode fiber 445. Thereafter, the light can be received by an optical detector (for example, a photodiode 424).

The rotary drive unit side of the optical rotary joint 403 is rotatably driven by a radial scanning motor 405 of the rotary drive device 404.

In accordance with an exemplary embodiment, an optical path length variable mechanism 432 for finely adjusting an optical path length of reference light can be disposed in the distal end opposite to the optical coupler 441 of the third single mode fiber 444.

In order for variations in the length of the individual probe unit 101 to be absorbed when the probe unit 101 is replaced and newly used, this optical path length variable mechanism 432 can be provided with optical path length changing means for changing an optical path length corresponding to the variations in the length of the individual probe unit 101.

In accordance with an exemplary embodiment, the third single mode fiber 444 and a collimating lens 418 are disposed on a single-axis stage 422 which is movable in an optical axis direction thereof as illustrated by an arrow 423, thereby forming the optical path length changing means.

In accordance with an exemplary embodiment, the single-axis stage 422 functions as the optical path length changing means having a variable range of the optical path length, which is long enough to absorb the variations in the optical path length of the probe unit 101 when the probe unit 101 is replaced. Furthermore, the single-axis stage 422 can also be provided with a function as adjusting means for adjusting an amount of offset. For example, even when the distal end of the probe unit 101 is not in close contact with the surface of the biological tissues, by finely changing the optical path length the single-axis stage with, light can be set to be in a state of interfering with the light reflected from the surface position of the biological tissues.

In accordance with an exemplary embodiment, the light whose optical path length is finely adjusted by the single-axis stage 422 and reflected on a mirror 421 via a grating 419 and a lens 420 is mixed with the light obtained from the first single mode fiber 440 side by the optical coupler 441 disposed in the middle of the third single mode fiber 444, and then is received by the photodiode 424.

Interference light received by the photodiode 424 in this way is photoelectrically converted, and is input to a demodulator 426 after being amplified by an amplifier 425. The demodulator 426 performs demodulation processing for extracting only a signal portion of the interference light, and an output therefrom is input to an A/D converter 427 as an interference light signal.

The A/D converter 427 performs sampling on the interference light signal, for example, at 90 MHz for 2048 points, and generates digital data (interference light data) of one line. In accordance with an exemplary embodiment, for example, the reason for setting the sampling frequency to 90 MHz is based on the assumption that approximately 90% of the wavelength swept cycles (25 μsec) are extracted as the digital data of 2048 points, when a repetition frequency of the wavelength sweeping is set to 40 kHz. However, the frequency is not particularly limited thereto.

The interference light data in the units of lines which is generated by the A/D converter 427 is input to a signal processing unit 428. The signal processing unit 428 generates data in a depth direction (line data) by performing frequency resolution on the interference light data using the fast Fourier transform (FFT), and the data is subjected to coordinate transformation. In this manner, an optical cross-sectional image is built at each intravascular position, and is output to the LCD monitor 113 at a predetermined frame rate (details to be described later).

The signal processing unit 428 is further connected to a control device of optical path length adjusting means 430. The signal processing unit 428 controls a position of the single-axis stage 422 via the control device of the optical path length adjusting means 430.

In accordance with an exemplary embodiment, the processing in the signal processing unit 428 is also realized in such a way that a predetermined program causes a computer to execute the processing.

4. Rotation Processing of Cross-Sectional Image

In the above-described configuration, if a user inputs an instruction to start scanning by operating the operation control apparatus 103, the signal processing unit 428 controls the scanner and pulling-back unit 102. In this manner, the imaging core 220 is rotated, and is moved in the longitudinal direction of the blood vessel by the imaging core 220 being pulled at a predetermined speed. As a result, as described previously, the A/D converter 427 outputs digitalized interference light data. Accordingly, the signal processing unit 428 can continuously build an optical cross-sectional image obtained at each position located along the movement direction of the imaging core 220, in a memory 428a belonging to the signal processing unit 428.

Figure 4:
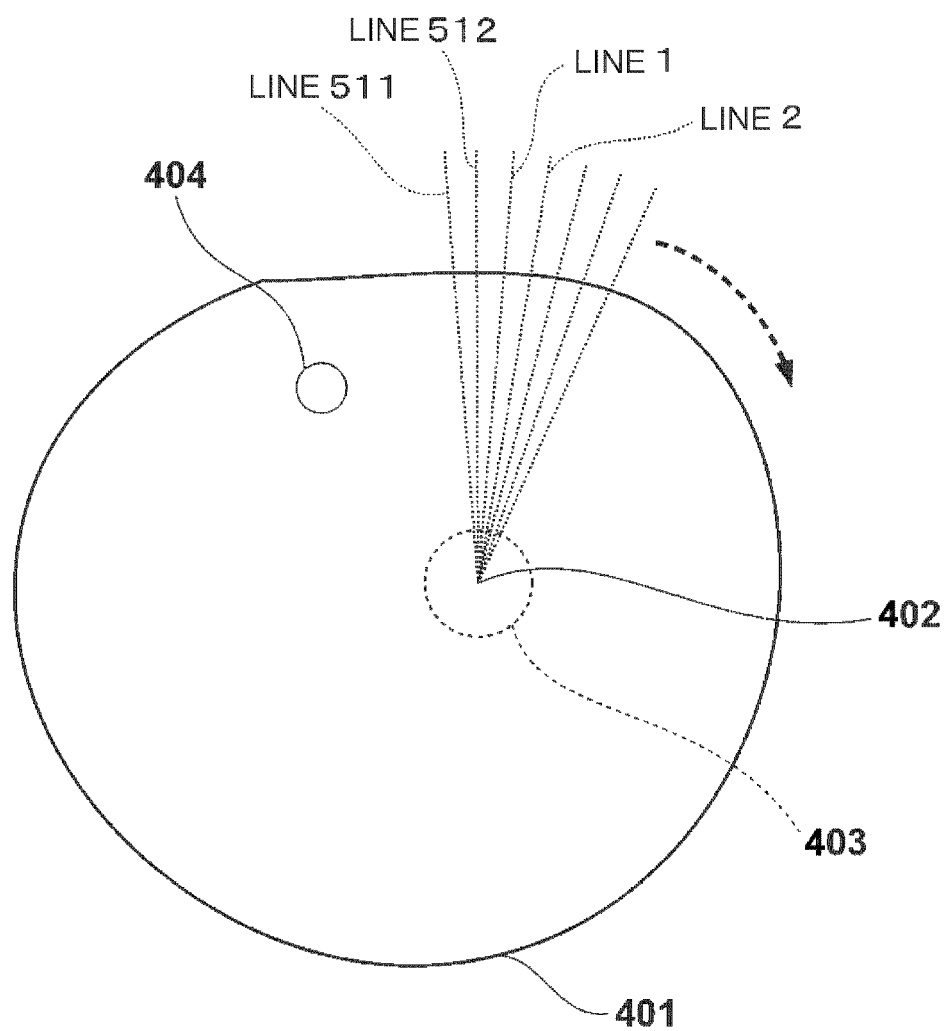
FIG. 4 is a view for describing reconfiguration processing of a cross-sectional image.

Here, processing for generating a single optical cross-sectional image will be described with reference to FIG. 4. FIG. 4 is a view for describing reconfiguration processing of the cross-sectional image of a blood vessel 401 where the imaging core 220 is located. While the imaging core 220 is rotated once (by 360 degrees), the measurement light is transmitted and received multiple times. In accordance with an exemplary embodiment, data of one line can be obtained in the light emitted direction by transmitting and receiving the light once. Accordingly, during one rotation, the light is transmitted and received 512 times, for example. In this manner, for example, data can be obtained for 512 lines, which extend radially from a rotation center 402. In the data of the 512 lines, the lines become dense in the vicinity of the rotation center position, and become isolated from each other as the lines are separated from the rotation center position. Therefore, pixels in the empty space between the respective lines are generated by performing known interpolation processing, thereby generating a two-dimensional image, which is visible to humans. The center position of the cross-sectional image coincides with the rotation center position of the imaging core 220. However, it should be noted that the center position of the cross-sectional image is not the center position of the cross section of the blood vessel.

When the light is transmitted and received, the light is reflected from the catheter sheath 201 itself. Accordingly, as illustrated in the drawing, a shadow 403 of the catheter sheath 201 is formed in the cross-sectional image. In addition, the illustrated reference number 404 represents a shadow of the guidewire 250. In practice, the guidewire 250 is made of metal, and the light is not transmitted therethrough. Accordingly, an image of a rear side portion of the guidewire 250 when viewed from the rotation center position cannot be obtained. It should be noted that the illustrated drawing is only a conceptual view.

In accordance with an exemplary embodiment, if a user inputs an instruction to start scanning by operating the operation control apparatus 103, the signal processing unit 428 controls the scanner and pulling-back unit 102. In this manner, the imaging core 220 is rotated, and is moved in the longitudinal direction of the blood vessel by the imaging core 220 being pulled at a predetermined speed (pulling-back processing). As a result, the signal processing unit 428 continuously builds multiple cross-sectional images obtained along the pulling direction of the imaging core 220, in its own memory 428a.

Figure 5A:
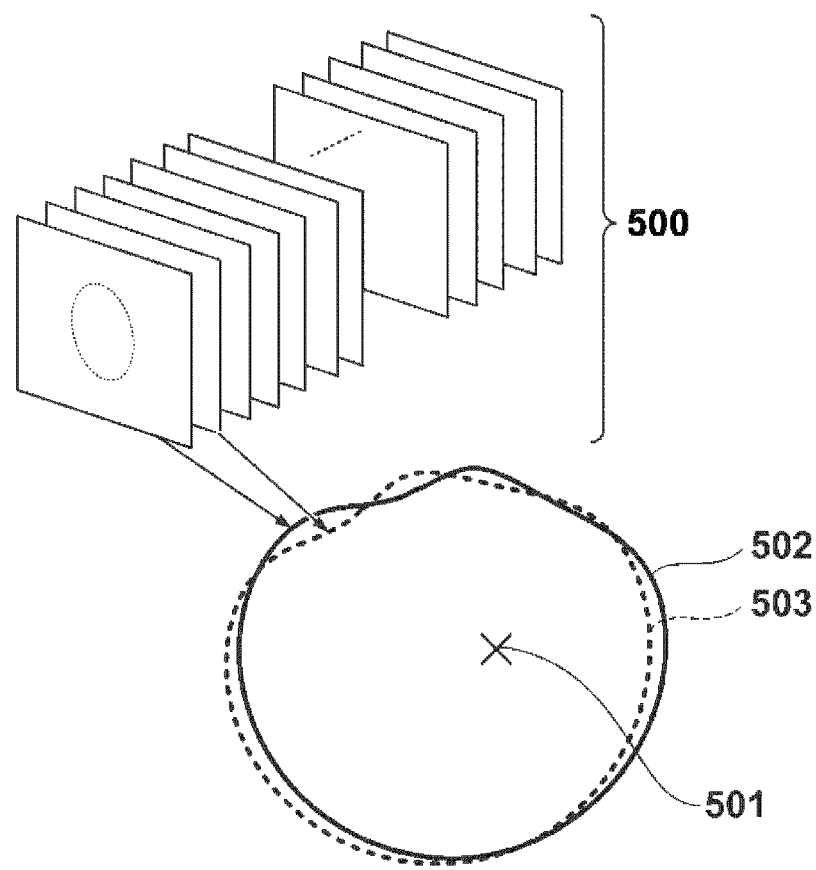
FIG. 5A is a view illustrating an example where the cross-sectional image becomes discontinuous due to fluctuations in rotation speed.
Figure 5B:
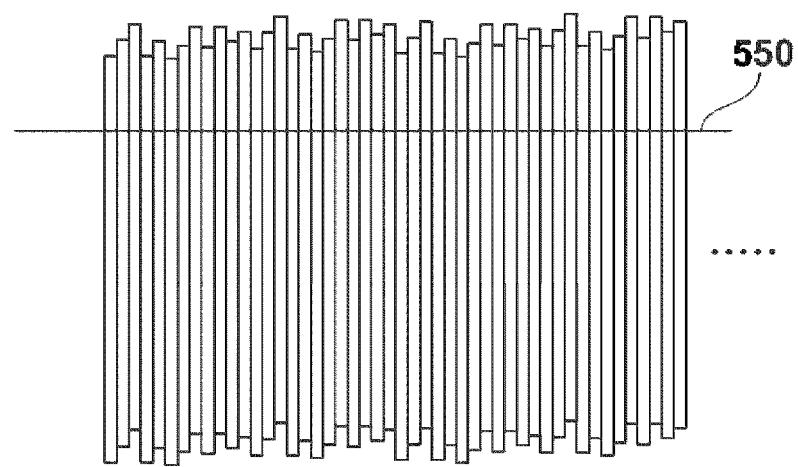
FIG. 5B is a view illustrating an image when a viewpoint is placed outside a three-dimensional image representing a vascular lumen surface, which is affected by the fluctuations in rotation speed.

The reference numeral 500 in FIG. 5A shows an example of the multiple cross-sectional images built in the memory 428a during the pulling-back processing. Here, when the imaging core 220 during the pulling-back processing is rotated at ideally constant speed, or at speed in an allowable range, the three-dimensional image of the intravascular wall can be configured by simply and sequentially connecting the cross-sectional images to one another. However, when the rotation speed of the imaging core 220 during the pulling-back processing is not constant and fluctuations exceeding the allowable range occur, a difference occurs in the orientation (rotation angle) in the cross-sectional images adjacent to each other. As a result, two images 502 and 503 adjacent to each other in the longitudinal direction of the blood vessel have a relationship of being twisted from each other. As a result, as illustrated by a solid line and a dashed line in the same drawing, even though the center positions are coincident with each other, the respective intravascular walls in the images 502 and 503 are discontinuous therebetween. If a vascular lumen surface formed when the respective cross-sectional images are connected to one another is viewed from the outside in a case where fluctuations in the rotation speed of the imaging core 220 continuously occur during the pulling-back processing period, an unnatural image is generated as illustrated in FIG. 5B. As a matter of course, even when the two-dimensional image split by a segment 550 in FIG. 5B is generated, rotation directions of the respective cross-sectional image are misaligned with each other. Consequently, the image cannot also become a smooth image.

According to the present exemplary embodiment, when the above-described three-dimensional image is configured, each rotation angle of the respective cross-sectional images is corrected, thereby generating the three-dimensional images which are smoothly continuous therebetween.

Herein, there can be a problem in that the fluctuations in the rotation speed of the imaging core 220 cannot be accurately recognized, and in that consequently, an accurate rotation angle for correcting the respective cross-sectional images cannot be obtained in order to coincide with an actual state of the blood vessel.

In accordance with an exemplary embodiment, a crossing portion (reference numeral 404 in FIG. 4) of the guidewire 250 is disclosed, which can always be present in the respective cross-sectional images. The guidewire 250 can be a single physical wire. Therefore, directions where the guidewire 250 can be present in two adjacent cross-sectional images (in case of FIG. 4, which direction of what number of lines) may be regarded as being the same as each other. In addition, the guidewire 250 has considerably higher light reflectance than biological tissues. Accordingly, it may be determined that the guidewire is present in a direction where the most reflective light is obtained in a line 512. For example, if the line having the most reflective light is in a line j, an angle θ thereof is expressed by the following equation.

$$\theta = 360 \times (j/\text{total number of lines})$$

(here, the total number of lines is 512 in the embodiment)

Alternatively, since the light is not transmitted therethrough in the rear of the guidewire, a low luminance layer spreads in the rear in the light emitting direction from a surface having a high luminance layer. The angle θ may be obtained by detecting that a very low luminance layer having uniform luminance is present immediately behind the high luminance layer.

In many cases, the stent still indwells the blood vessel after treatment. The stent can be generally configured to include metal. Accordingly, the light can be totally reflected on the surface of the stent, and is not transmitted therethrough. For example, luminance distribution of a line where the stent is present is similar to the luminance distribution of the guidewire. Accordingly, when the guidewire is detected by using the above-described method for one cross-sectional image, there is a possibility that the stent may be erroneously detected as the guidewire.

Normally, the stent indwells only a treatment target region. The pulling-back can be performed in a range exceeding the treatment target region in order to observe the entire treatment target region. For example, the guidewire can be detected over the entire pulling-back area, and the stent or the like appears only in a specific region excluding both ends of the pulling-back area. Processing for distinguishing between the guidewire and the stent can be performed as follows by utilizing the above-described characteristics.

First, over the entire pulling-back area, a line which may be determined as the previously described metal is obtained as a guidewire candidate point from the respective cross-sectional images. A candidate point obtained from an interest cross-sectional image is compared with a candidate point detected from the adjacent cross-sectional image, and grouping is performed by detecting candidate points in which positions of the candidate points are closest. This processing is repeatedly performed from a start position of the pulling-back or an end position of the pulling-back, thereby calculating the candidate points over the entire pulling-back area. These candidate points are recognized as the guidewire.

For example, if a light emitting direction r and an angular direction θ are used as a position when the above-described processing is applied, there is a possibility that the closest candidate point detected from the cross-sectional image where the stent still indwells and a rotation phenomenon occurs may be erroneously detected as the stent. In order to avoid this problem, weighting factors are respectively added to a distance r and a distance θ so as to calculate the distance r and the distance θ, when the position closest to the rotation axis is detected.

$$\Delta L_i = \sqrt{K_1(r_{i,a} - r_{i-1,j})^2 + K_2(\theta_{i,a} - \theta_{i-1,j})^2}$$

However, the expression indicates a=0 to m, m represents the guidewire candidate point detected in the $i^{th}$ frame, and $r_{i,j}$ and $\theta_{i,j}$ represent the $j^{th}$ position coordinates, for example, a radial position and an angular position, of multiple guidewire candidate points detected from a start frame of the pulling-back to the $i^{th}$ frame. K1 and K2 represent weighting factors.

$\Delta L_i$ calculated by the above-described expression is set to an evaluation function, a value of a in which $\Delta L_i$ has the minimum value, for example, $(r_{i,b}, \theta_{i,b})$ is obtained in case of (a=b), and the guidewire candidate point is determined as a representative guidewire point. i is applied from the start frame of the pulling-back to the end frame of the pulling-back, thereby obtaining collective positions (R, θ) of the representative guidewire point in all frames. Normally, the stent is not present in the start position of the pulling-back. Accordingly, the guidewire candidate point is uniquely determined. Normally, the stent indwells so as to be in close contact with the blood vessel, and the guidewire is present in a random point in the vascular lumen. For example, the guidewire is more frequently present in the vicinity of the imaging core than the stent. In addition, in the cross-sectional image, images are rotated in the frames adjacent to each other due to the influence of heartbeats or the like. As described above, correlation between the guidewire positions in the adjacent frames is higher in the direction r than in the direction θ. In view of this point, the weighting factors are set such that $K_1 > K_2$. In this manner, a much higher detection rate of the guidewire can be obtained.

In addition, in a case where the rotation correction of the cross-sectional images is performed, when the $i^{th}$ cross-sectional image is represented by F(i) and an angle where the guidewire 250 is present in the cross-sectional image F(i) is represented by θ(i), the rotation correction is performed so that the guidewire 250 has a preset target angle Est. In this case, a rotation angle Δθ is expressed by the following equation.

$$\Delta\theta = \theta st - \theta(i)$$

For example, if it is assumed that a target angle θst=90° (direction of 0 o'clock in a timepiece is set to 0°), when the angle in the direction where the guidewire 250 is present with respect to the center position of the interest cross-sectional image is 80°, the interest cross-sectional image is rotated by 10° (=90−80).

Figure 6:
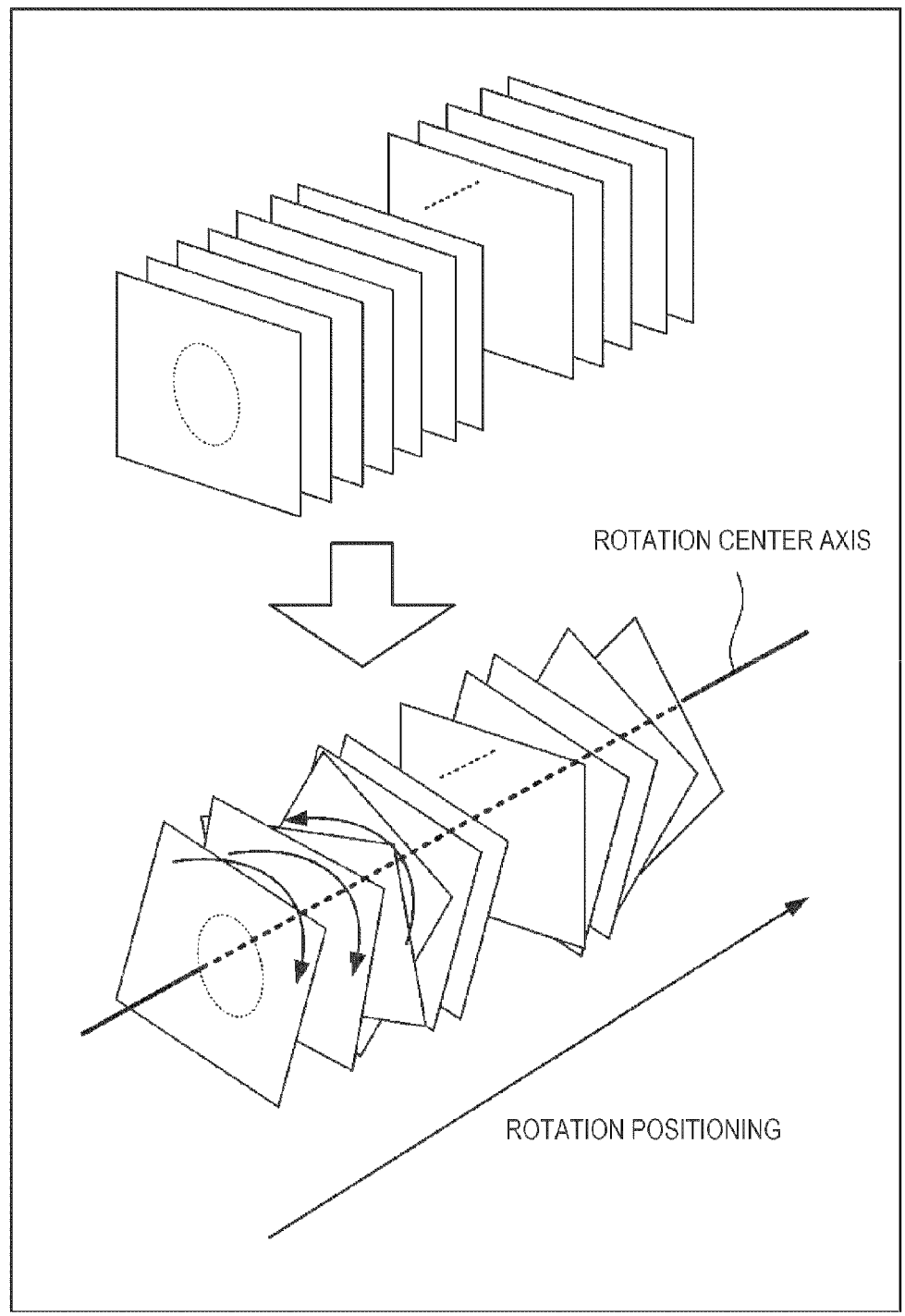
FIG. 6 is a view for describing rotation processing according to the exemplary embodiment.

In practice, as illustrated in FIG. 6, the rotation correction is performed on all of the multiple cross-sectional images obtained through the pulling-back in order to cause the direction where the guidewire 250 is present to coincide with the preset direction. As compared to that in FIG. 5B, the three-dimensional image obtained by connecting the cross-sectional images to one another is much smoother. Accordingly, the three-dimensional image is reproduced into a natural image. This means that the three-dimensional image obtained after the rotation correction as described above shows a state closer to the actual state of the blood vessel than the three-dimensional image in FIG. 5B, and can contribute to a correct diagnosis.

Figure 7:
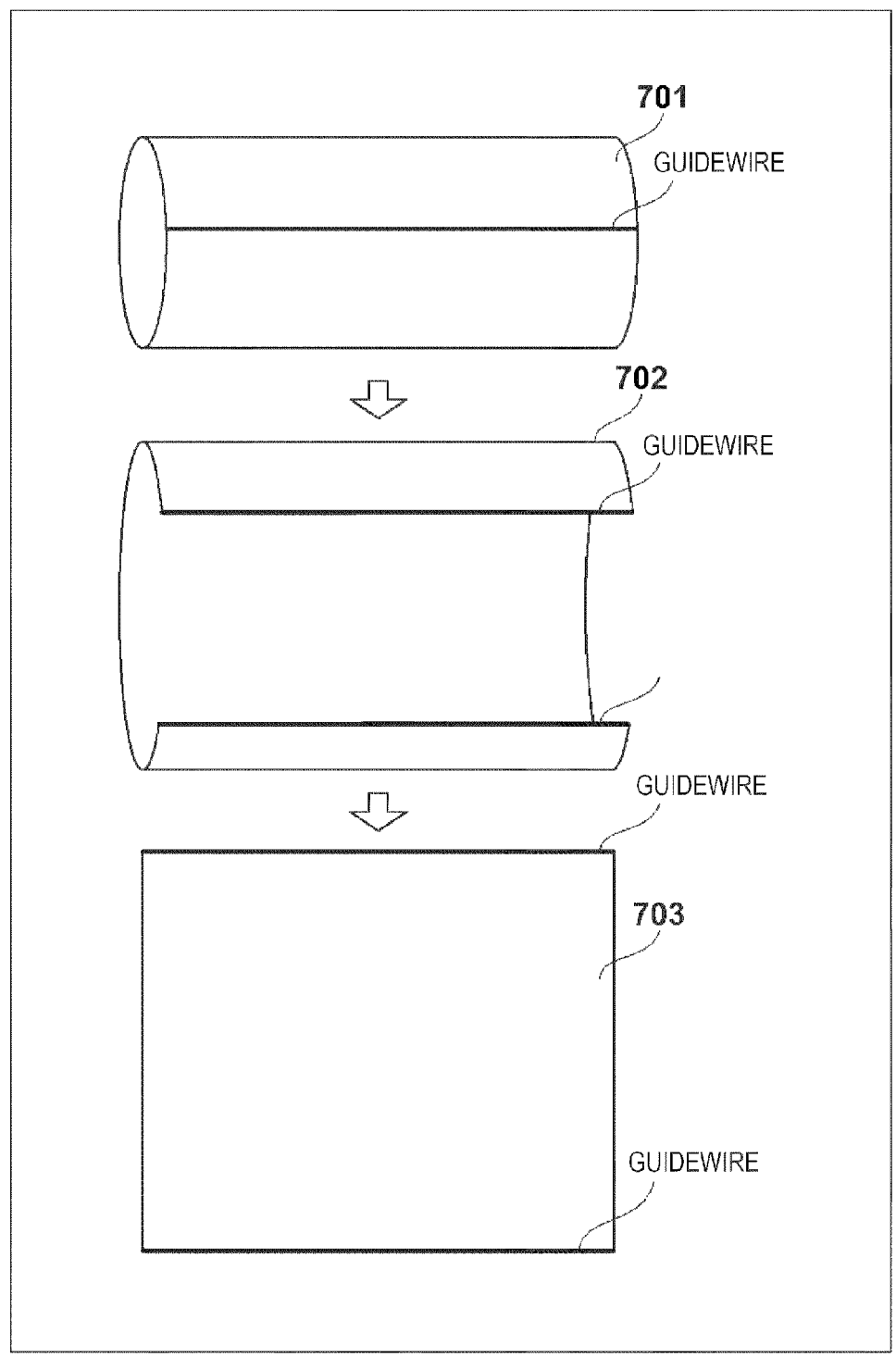
FIG. 7 is a view for describing a development display of an intravascular wall according to the exemplary embodiment.

Furthermore, when the three-dimensional image is generated for the blood vessel after the rotation correction as described above, directions in which a shadow (guidewire image) of the guidewire 250 is present in the respective cross-sectional images are coincident with each other. Accordingly, the three-dimensional image which can be obtained is generated as illustrated by the reference numeral 701 in FIG. 7. The guidewire image also has a linear shape parallel to a cylindrical axis. Therefore, if an image 702 is obtained by spreading the guidewire to cutting ends and then an image 703 is reconfigured, the image has a substantially rectangular shape similar to the shape of a display screen. Moreover, the cutting ends can be pushed away to an upper side and a lower side of the rectangular shape. Therefore, a user can view the image 703 presented as if the guidewire image which obstructs a user's view during diagnosis is removed.

5. Description of Processing Procedures

Figure 8:
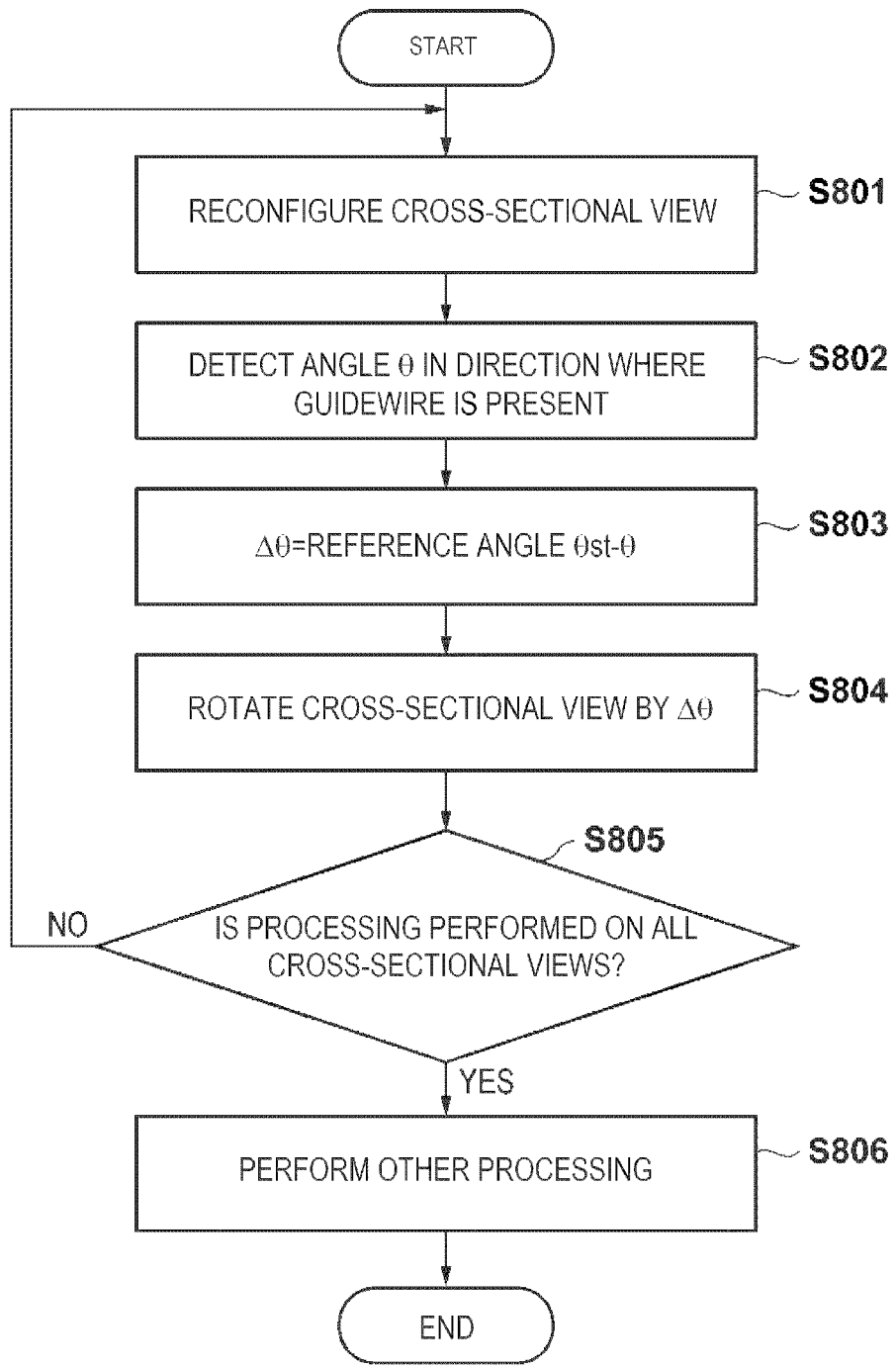
FIG. 8 is a flowchart illustrating processing procedures relating to rotation correction of a cross-sectional image for building a three-dimensional image according to the exemplary embodiment.

The signal processing unit 428 which completes the pulling-back processing may eventually generate the respective cross-sectional images in accordance with a flowchart illustrated in FIG. 8. Hereinafter, referring to the same drawing, processing of the signal processing unit 428 will be described. In practice, processing procedures in accordance with the flowchart in the same drawing are stored in a hard disk device or the like as a program, which causes the signal processing unit to execute the signal processing.

First, in Step S801, a single cross-sectional image is reconfigured by performing the pulling-back processing. The reconfiguration processing is known, and thus description thereof will be omitted herein.

Next, in Step S802, the angle θ in the direction where the guidewire is present with respect to the center position (corresponding to the position of the rotation axis of the imaging core 220) of the reconfigured cross-sectional image is obtained. As previously described, the guidewire 250 has much higher light reflectance than biological tissues. Accordingly, the angle θ may be obtained, based on the line where data showing the most intensive reflected light is present within each line data (line 512 in the embodiment) used when the cross-sectional image is reconfigured. When the stent is arranged inside the blood vessel, the above-described equation is evaluated, and the position of the guidewire 250 is specified. Then, the angle θ in the direction where the guidewire is present in the respective tomographic images may be obtained.

Next, in Step S803, a difference Δθ between the pre-established target angle θst and the obtained angle θ can be calculated. Then, in Step S804, the cross-sectional image reconfigured in previous Step S801 is rotated around the center position of the cross-sectional image as the rotation center by the amount of the calculated difference Δθ.

Thereafter, in Step S805, it is determined whether or not the above-described processing is performed on all of the cross-sectional images which have to be reconfigured through the pulling-back. If the result is determined to be No, the processing from Step S801 to Step S805 is repeatedly performed.

If it is determined that the rotation correction processing is completed for all of the cross-sectional images, the processing proceeds to Step S806. The respective cross-sectional images after the rotation correction are connected to one another so that the rotation center positions are coincident with one another. In this manner, the three-dimensional image is built, and this processing is completed.

Thereafter, the three-dimensional image is displayed or the respective cross-sectional images are displayed via various user interfaces, for example. However, the displays may be performed, based on the cross-sectional image after the above-described rotation correction and the three-dimensional image obtained from the cross-sectional image after the rotation correction. Accordingly, the subsequent description will be omitted. However, although described previously, according to the present embodiment, as described with reference to FIG. 7, the guidewire image can be obtained as a straight line parallel to the axis of the three-dimensional blood vessel image. Therefore, when the two-dimensional image split in the longitudinal direction of the blood vessel is displayed, it is desirable to display an image split along the guidewire.

As described above, according to the present exemplary embodiment, the three-dimensional image can be generated with higher quality than ever before by preventing the quality of the three-dimensional image from becoming poor due to the fluctuations in the rotation speed of the imaging core 220 which performs scanning in order to obtain the cross-sectional image.

In the embodiment, the OCT has been described as an example, but the embodiment can also be applied to the IVUS. Even in the IVUS, since the guidewire has higher reflection intensity of the ultrasound as compared to biological tissues, the guidewire and the biological tissues can be distinguished, similarly to in the above-described embodiment. Therefore, the rotation correction of the respective cross-sectional images can be performed.

In addition, as is understood from the above-described embodiment, the reconfiguration of the cross-sectional image and the reconfiguration processing of the three-dimensional image are performed by the signal processing unit 428 configured to include a microprocessor. The microprocessor realizes its function by using an executable program. As a matter of course, the program also falls within the scope of the present invention. In addition, the program is normally executable by being stored in a computer-readable storage medium such as a CD-ROM, a DVD-ROM, or the like, by being set in a reading device (CD-ROM drive or the like) belonging to a computer, and by being copied to or installed in a system. Accordingly, it is apparent that the related computer-readable storage medium also falls within the scope of the present invention.

Without being limited to the above-described embodiment, the present invention can be changed and modified in various ways without departing from the gist and the scope of the present invention. Therefore, in order to apprise the public of the scope of the present invention, the following Claims are appended herein.

The detailed description above describes an imaging apparatus for diagnosis, information processing apparatus, and control method thereof, program thereof, and computer-readable storage medium thereof. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. An imaging apparatus for diagnosis which reconfigures a three-dimensional image of biological tissues in such a way that a probe which has a sheath for accommodating an imaging core emitting a signal toward the biological tissues and detecting a reflected signal thereof and whose distal end has a guidewire lumen for guiding the imaging core to the biological tissues, and a guidewire passing through the inside of the guidewire lumen are used so as to move and rotate the imaging core along the sheath, the imaging apparatus for diagnosis comprising:
a processor configured to:
generate a cross-sectional image at each axial position of the movement, based on data obtained via the imaging core by a movement and rotation of the imaging core inside the sheath;
detect a direction in which the guidewire is present in each of the cross-sectional images;
rotate a target cross-sectional image detected in accordance with an angular difference between the direction in which the guidewire is present and a preset direction in the target cross-sectional image, for each of the cross-sectional images;
generate the three-dimensional image along the movement direction from each of the cross-sectional images which are previously rotated; and
generate a two-dimensional image, which includes a segment representing the guidewire in the three-dimensional image on each of an upper side and a lower side of the two-dimensional image.

2. The imaging apparatus for diagnosis according to claim 1,
wherein the data obtained by the rotation of the imaging core and the direction in which the guidewire is present is based on a value indicating reflected signal intensity.

3. The imaging apparatus for diagnosis according to claim 1, further comprising:
a display apparatus configured to display the two-dimensional image, wherein the guidewire is on the top side and the lower side of the two-dimensional image.

4. The imaging apparatus for diagnosis according to claim 1, wherein the preset direction is an angle of 90 degrees, and a direction of 0 degrees is equal to 0 o'clock in a timepiece.

5. The imaging apparatus for diagnosis according to claim 1, wherein the direction of the guidewire is detect in each of the cross-sectional images is a guidewire image having a linear shape, which is parallel to a cylindrical axis.

6. A control method of an imaging apparatus for diagnosis which reconfigures a three-dimensional image of biological tissues in such a way that a probe which has a sheath for accommodating an imaging core emitting a signal toward the biological tissues and detecting a reflected signal thereof and whose distal end has a guidewire lumen for guiding the imaging core to the biological tissues, and a guidewire passing through the inside of the guidewire lumen are used so as to move and rotate the imaging core along the sheath, the control method comprising:

generating a cross-sectional image at each axial position of the movement, based on data obtained via the imaging core by a movement and rotation of the imaging core inside the sheath;

detecting a direction where the guidewire is present in each of the cross-sectional images;

rotating a target cross-sectional image detected in the detection step in accordance with an angular difference between the direction in which the guidewire is present and a preset direction in the target cross-sectional image, for each of the cross-sectional images;

generating the three-dimensional image along the movement direction from each of the cross-sectional images which are previously rotated; and generating a two-dimensional image, which includes a segment representing the guidewire in the three-dimensional image on each of an upper side and a lower side of the two-dimensional image.

7. The control method according to claim 6, comprising: referring to the data obtained by the rotation operation of the imaging core, and detecting the direction in which the guidewire is present, based on a value indicating reflected signal intensity.

8. The control method according to claim 6, further comprising:
displaying the two-dimensional image on a display, wherein the guidewire is on the top side and the lower side of the two-dimensional image.

9. The control method according to claim 6, wherein the preset direction is an angle of 90 degrees, and a direction of 0 degrees is equal to 0 o'clock in a timepiece.

10. The control method according to claim 6, comprising: detecting the direction of the guidewire in each of the cross-sectional images as a guidewire image having a linear shape, and wherein the linear shape is parallel to a cylindrical axis.

11. An information processing apparatus that generates a three-dimensional image, based on data from an imaging core, which is obtained by an imaging apparatus for diagnosis that uses a probe which has a sheath for accommodating the imaging core emitting a signal toward the biological tissues and detecting a reflected signal thereof and whose distal end has a guidewire lumen for guiding the imaging core to the biological tissues, and a guidewire passing through the inside of the guidewire lumen so as to move and rotate the imaging core along the sheath, the information processing apparatus comprising:

a processor configured to:
generate a cross-sectional image at each axial position of a movement, based on the data obtained via the imaging core;
detect a direction in which the guidewire is present in each of the cross-sectional images;
rotate a target cross-sectional image detected by the detection means in accordance with an angular difference between the direction in which the guidewire is present and a preset direction in the target cross-sectional image, for each of the cross-sectional images;
generate the three-dimensional image along the movement direction from each of the cross-sectional images which are previously rotated; and
generate a two-dimensional image, which includes a segment representing the guidewire in the three-dimensional image on each of an upper side and a lower side of the two-dimensional image.

12. The imaging apparatus for diagnosis according to claim 11, wherein the data obtained by rotation of the imaging core and the direction in which the guidewire is present is based on a value indicating reflected signal intensity.

13. The imaging apparatus for diagnosis according to claim 11, further comprising:
a display apparatus configured to display the two-dimensional image, wherein the guidewire is on the top side and the lower side of the two-dimensional image.

14. The imaging apparatus for diagnosis according to claim 11, wherein the preset direction is an angle of 90 degrees, and a direction of 0 degrees is equal to 0 o'clock in a timepiece.

15. The imaging apparatus for diagnosis according to claim 11, wherein the direction of the guidewire is detect in each of the cross-sectional images is a guidewire image having a linear shape, which is parallel to a cylindrical axis.

16. A control method of an information processing apparatus that generates a three-dimensional image, based on data from an imaging core, which is obtained by an imaging apparatus for diagnosis that uses a probe which has a sheath for accommodating the imaging core emitting a signal toward the biological tissues and detecting a reflected signal thereof and whose distal end has a guidewire for guiding the imaging core to the biological tissues, so as to move and rotate the imaging core along the sheath, the control method comprising:

generating a cross-sectional image at each axial position of a movement, based on the data obtained via the imaging core;
detecting a direction in which the guidewire is present in each of the cross-sectional images;
rotating a target cross-sectional image detected in the detection step in accordance with an angular difference between the direction in which the guidewire is present and a preset direction in the target cross-sectional image, for each of the cross-sectional images;
generating the three-dimensional image along the movement direction from each of the cross-sectional images which are previously rotated; and
generating a two-dimensional image, which includes a segment representing the guidewire in the three-dimensional image on each of an upper side and a lower side of the two-dimensional image.

17. The control method according to claim 16, comprising:
referring to the data obtained by the rotation operation of the imaging core, and detecting the direction in which the guidewire is present, based on a value indicating reflected signal intensity.

18. A program that is read by a computer, and that causes a computer to execute the control method according to claim 16.

19. A non-transitory computer-readable storage medium that stores the program according to claim 18.

20. The control method according to claim 16, further comprising:
displaying the two-dimensional image on a display, wherein the guidewire is on the top side and the lower side of the two-dimensional image.

* * * * *